US008495011B2

(12) United States Patent
Sanders et al.

(10) Patent No.: US 8,495,011 B2
(45) Date of Patent: Jul. 23, 2013

(54) SYSTEM AND METHOD FOR MANAGEMENT OF RESEARCH SUBJECT OR PATIENT EVENTS FOR CLINICAL RESEARCH TRIALS

(75) Inventors: Todd B. Sanders, Austin, TX (US);
Lance D. Nickens, Austin, TX (US);
Carl T. Wibbenmeyer, Austin, TX (US)

(73) Assignee: The Patient Recruiting Agency, LLC, Austin, TX (US)

( * ) Notice: Subject to any disclaimer, the term of this patent is extended or adjusted under 35 U.S.C. 154(b) by 417 days.

(21) Appl. No.: 12/187,197

(22) Filed: Aug. 6, 2008

(65) Prior Publication Data
US 2009/0043817 A1 Feb. 12, 2009

Related U.S. Application Data

(60) Provisional application No. 60/964,032, filed on Aug. 8, 2007.

(51) Int. Cl.
*G06F 7/00* (2006.01)
*G06F 17/00* (2006.01)

(52) U.S. Cl.
CPC . *G06F 7/00* (2013.01); *G06F 17/00* (2013.01)
USPC ............ 707/610; 707/618; 707/624; 707/661

(58) Field of Classification Search
None
See application file for complete search history.

(56) References Cited

U.S. PATENT DOCUMENTS

| 2002/0046054 A1* | 4/2002 | Morand et al. ..................... 705/1 |
| 2002/0095585 A1* | 7/2002 | Scott ............................. 713/185 |
| 2005/0055244 A1* | 3/2005 | Mullan et al. ..................... 705/2 |
| 2005/0065817 A1* | 3/2005 | Mihai et al. ....................... 705/2 |
| 2005/0080721 A1* | 4/2005 | Kearney et al. ................. 705/38 |
| 2006/0143047 A1 | 6/2006 | Briegs et al. |
| 2007/0106754 A1 | 5/2007 | Moore |
| 2007/0178501 A1* | 8/2007 | Rabinowitz et al. ............. 435/6 |
| 2007/0266030 A1* | 11/2007 | Bradley et al. .................. 707/10 |
| 2008/0014567 A1* | 1/2008 | Schlachta-Fairchild ...... 434/262 |

OTHER PUBLICATIONS

Sanders et al., A quantitative cardiac angiography system for use in a clinical trial, Proceedings Computers in Cardiology 1988, Sep. 25-28, 1988, pp. 543-546, Washington DC, ISBN: 0-8186-1949-X.*
Jatinder et al., Web-based submission, archive, and review of radiotherapy data for clinical quality assurance: a new paradigm, Int. J. Radition Oncology Biol. Phys., vol. 57, No. 5, pp. 1427-1436, 2003.*
U.S. Appl. No. 60/816,907, filed Jun. 27, 2006.*

* cited by examiner

*Primary Examiner* — Jay Morrison
(74) *Attorney, Agent, or Firm* — DuBois, Bryant & Campbell, LLP; William D. Wiese

(57) ABSTRACT

A system and method for managing clinical research trials is disclosed. The system and method may include a centralized secure database with information on clinical research trial participants, clinical research trial events, investigator and administrator inputs, and communication of participants, investigators and administrators. In one embodiment, the system and method allows investigators to contact participants without disclosing confidential contact information of the participants to the investigators by storing health information and contact information in separate databases. In one embodiment, administrators may access clinical research trial information through a secure web portal.

12 Claims, 1 Drawing Sheet

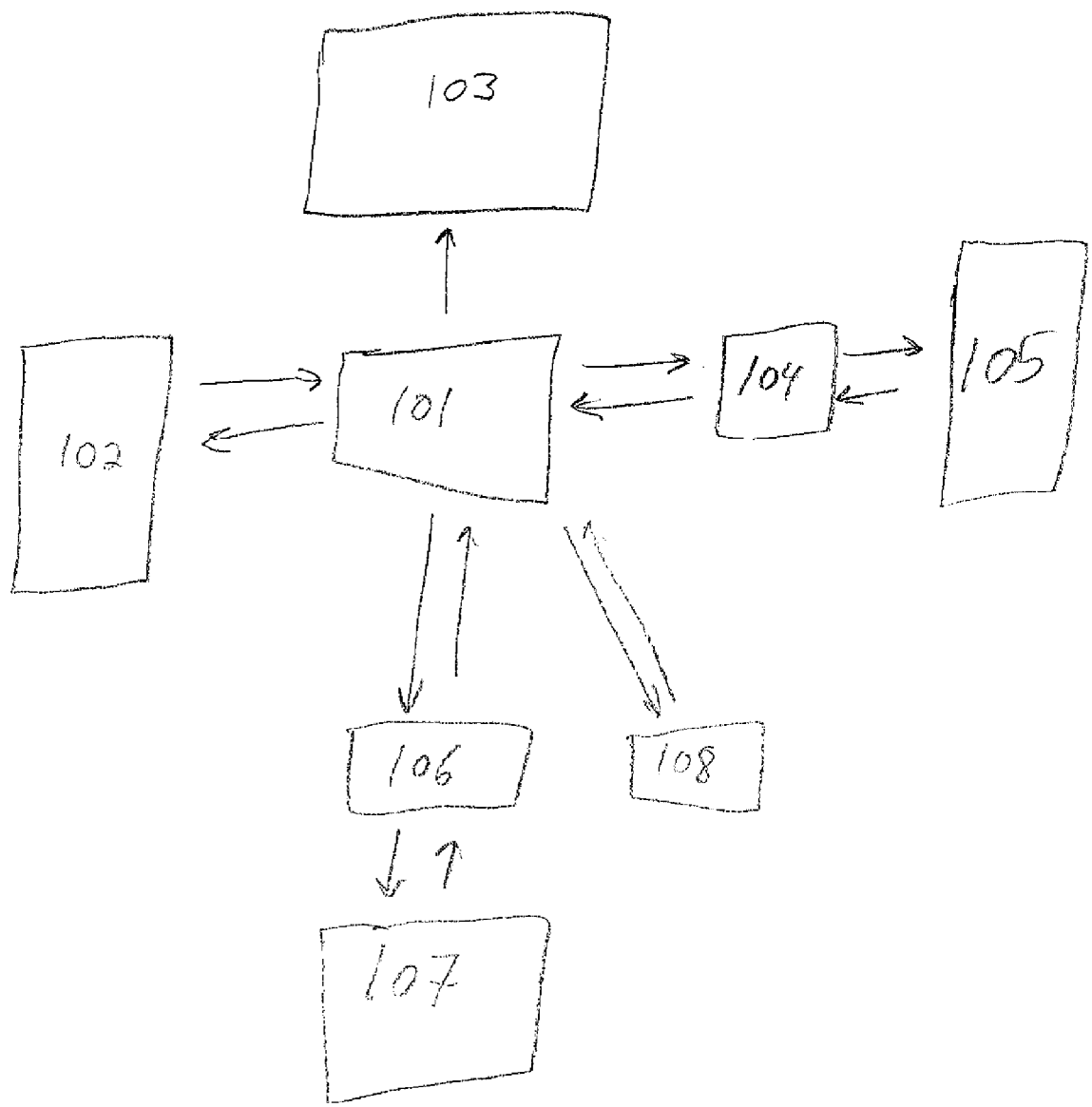

SYSTEM AND METHOD FOR MANAGEMENT OF RESEARCH SUBJECT OR PATIENT EVENTS FOR CLINICAL RESEARCH TRIALS

CROSS-REFERENCE TO RELATED APPLICATIONS

This non-provisional application claims priority based upon prior U.S. Provisional Patent Application Ser. No. 60/964,032 filed Aug. 8, 2007, entitled "A system and method of using internet web portals to monitor and manage patient events, including appointments, for clinical research trials," the disclosure of which is fully incorporated herein by this reference as if fully set forth herein in its entirety.

BACKGROUND

The present invention relates generally to clinical research trials and, more particularly, to a system and method for managing patient events, including appointments. The terms "research subjects" and "patients" are used interchangeably throughout.

The scientific value of clinical research trials significantly depends on the careful management of a large number of people and events to ensure, for example, that specific events occur within specific time ranges (i.e. clinic visits occur within certain time parameters) and that the results from such events (i.e. enrollment, withdrawal or continuation, for example) are properly recorded and monitored. Events may include any occurrence related to the administration of a clinical research trial, such as appointments, and even engendering the goodwill of participants like sending birthday cards or small gifts of appreciation.

The people involved in a clinical research trial can be generally grouped into three classes: administrators, investigators, and participants. Administrators may include the sponsor of the study or management of the clinical research organization who oversee and implement a clinical research trial. Investigators include the independent physicians conducting the research and their employees. One principal responsibility of investigators and administrators is to track and manage the participants in a clinical research trial. Participants may include individuals from the general public who have voluntarily agreed to participate in a clinical research trial and have been screened to verify that they satisfy any necessary criteria for participation.

A single clinical research trial may involve a number of investigators who are each conducting the trial relative to a set of participants. At the same time, the confidentiality requirements of clinical research trials often prevent certain administrators from obtaining personal information of participants, such as the participants' name and contact information, even though the use of such information may be necessary. For this and other reasons, systems and methods known in the art for managing clinical research trials are often expensive and can compromise the success of the clinical research trial through insufficient documenting and recording of events, errors in the dispensing of the clinical trial protocol, and insufficient and untimely communication of the status of the clinical research trial as it is being implemented to allow for corrective adjustments. Therefore, it can be appreciated that there is a need for a system and method for managing patient events for clinical research trials that is inexpensive and will provide a convenient and timely means for monitoring, documenting, recording, and communicating relevant aspects of a clinical research trial for and between administrators, investigators, and participants without compromising confidentiality. The present invention provides these and other advantages, as will be apparent from the following detailed description and accompanying figures.

BRIEF SUMMARY OF THE INVENTION

The system and method described herein relate to the management of patient events for clinical research trials. One embodiment of the present invention includes a centralized secure database, an administrator database, and one or more investigator databases. The administrator database and the one or more investigator databases are communicatively connected to the centralized secure database. This connection allows information to be periodically transferred from the administrator database and the one or more investigator databases to the centralized secure database. This embodiment also includes at least one communication gateway and three separate interfaces: (i) a high-clearance interface for accessing the centralized secure database, (ii) an administrator interface for accessing the administrator database, and (iii) an investigator interface for accessing the one or more investigator databases.

An objective of the present invention is to facilitate communication between administrators and investigators and between investigators and participants, including direct electronic communication between investigators and participants without providing such administrators access to confidential contact information of such participants. Additionally, an objective of the present invention is to assist investigators with tracking and managing participants by, for example, providing investigators with automated scheduling and data recording capabilities. Further, an objective of the present invention is to provide administrators and investigators the ability to monitor and adjust a clinical research trial during the implementation of the clinical research trial. Still further, an objective of the present invention is to automatically compile the communication and other information related to the implementation of a clinical research trial to allow for more accurate and faster analysis of the progress of the clinical research trial. Even further, an objective of the present invention is to reduce the costs and errors currently associated with clinical research trials in a manner that remains compliant with applicable confidentiality laws, such as the Health Insurance Portability and Accountability Act (HIPAA). Even further yet, an objective of the present invention is to record the reasons why prospective participants do not qualify for participation in a clinical research trial.

For all these reasons, and many others, the system and method of the present invention represents an innovation in the field of clinical research trials.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 1 is a diagram depicting the flow of information through one embodiment of the present invention.

DETAILED DESCRIPTION

The system and method described herein relate to the management of patient events for clinical research trials. In one embodiment, configuration information of a clinical research trial is received from at least two sources. First, trial dependent configuration information may be received from an administrator. For example, trial dependent configuration information might include a requirement that each enrolled participant have three (3) appointments with an investigator over the life of the trial and that each appointment occur within a specified number of days after the date of the participant's enrollment or randomization into the trial. The trial dependent configuration information might also include the identity information of each investigator and an assignment of a login and password for each investigator. In one embodiment, an administrator or super-administrator enters the trial dependent configuration information into a centralized database that is secured from intrusion and web accessible via a secured encrypted protocol.

Second, configuration information may also be received from investigators or directly from participants. For example, a participant may be given the opportunity to affirmatively consent to his participation in a clinical research trial after he has received a disclosure of the trial attributes. Participants may also be given the opportunity to directly enter their personal information. Under certain circumstances, investigators may alternatively collect certain personal information from prospective or accepted participants. This personal information, also known as "limited use data", should contain no more personally identifiable information that is permitted by applicable regulation and may include the reasons why a prospective participant qualifies or does not qualify for participation in a particular clinical research trial. The configuration information to be received from investigators may also include the date of a participant's enrollment and the random assignment of a particular participant into a particular trial sub-group within a clinical research trial. In one embodiment, investigators are provided with proxy contact information to separate the data in different databases to ensure confidentiality.

In one embodiment, the present invention tracks events by, for example, automatically providing prompts of pending events to administrators, investigators and/or participants. An administrator, investigator and/or participant may also be prompted to provide an update upon the occurrence of a scheduled event date. The nature and type of prompting may vary depending upon the event. For example, if the event is an office visit, the prompt may be directed to an investigator and consist of a request for confirmation that the participant attended the visit and for the results of that visit. A prompt may include notifications and alarms sent via email, pop-up, text message or other forms of communication and prompts may be weighted as to their relative importance. For example, if a particular participant has not been scheduled for an appointment within a pre-determined number of days, an urgent prompt may be sent to an investigator. Similarly, if an enrolled participant has not been scheduled for an appointment during an applicable appointment window, a critical prompt may be sent to an investigator.

In one embodiment of the present invention, participants may elect to receive prompts, such as an email, text, reminder postcard, and/or phone reminders of office visit appointments, subject to the approval of an investigator. Such participants may also be given the option to respond to such prompts. For example, a reminder email, text message, or phone call may include a website address that allows a participant to confirm whether the participant can attend a scheduled appointment and, if not, the participant may be allowed to reschedule the appointment or a prompt may be sent to the investigator in the form of a reminder to directly contact such participant for rescheduling.

In one embodiment, the present invention also includes useful tools for performing such tasks as sorting, searching, calendaring, and statistically analyzing information. For example, the data received from investigators may be stripped of all personally identifiable information and presented to an administrator through a website portal. The administrator may elect to analyze such data on an aggregate basis for the entire clinical research trial or a portion of the clinical research trial, or on an investigator-by-investigator basis. Certain critical data may also automatically be presented to investigators or administrators in a report format. Such reports may include, for example, the reasons for participants' early withdrawal from a trial, the reasons for participants' ineligibility for a particular trial, the number of appointments that have been attended or not attended within established visit windows, and the number and rates of protocol violations in the aggregate and with respect to individual investigators. An investigator or administrator may also sort information stored for participants to identify events that are at risk of not being completed timely.

In one embodiment, the present invention allows administrators to communicate with each investigator, all investigators or a sub-group of investigators. This feature, in combination with reporting features such as those described in the preceding paragraph, provides administrators and investigators the ability to react to and remedy potential shortfalls in a trial during the administration of the trial. For example, communication may consist of a pop-up window upon a log-in by the investigator and may include instructions or a request for the investigator to perform certain tasks or provide the administrator with certain information. Such instructions or requests may require an investigator to email certain specified information to a designated party or respond with information to the party initiating a request. A confidential log of all communications may be kept for reference. In addition, an investigator may post a question to be answered by an administrator, and the administrator may elect for the response to be sent to only the instigator asking the question or to be posted to all investigators or a sub-group of investigators.

For security, an embodiment of the present invention may use a password protected encrypted protocol. The passwords may be changed by each user and may not be recovered within the database. In the event of a lost password, an administrator may reset the password. In one embodiment, the present invention may also record each data entry or change to the database and record the date, time and login of a party making a change to the database.

Referring now to FIG. 1, a Centralized Secure Database 101 sends and receives information to and from an Administrator Database 104 and one or more Investigator Databases 106. Periodically, the Centralized Secure Database 101 is synched with Administrator Database 104 and each Investigator Database 106. In one embodiment, however, the Administrator Database 104 and each Investigator Database 106 contain only limited datasets in order to restrict administrators and investigators access to restricted information. For example, personal information of a participant may be entered into an Investigator Database 106 and subsequently transferred to the Centralized Secure Database 101 so that the information is no longer accessible to the Investigator Database 106 and is never accessible to the Administrator Database 104.

An investigator may access a secure web portal 107 to enter information into an Investigator Database 106 corresponding to that investigator. Such information may include limited use data for each participant assigned to that investigator, such as contact information for automated appointment reminders if the participant has consented to receiving such automated reminders. The investigator may also enter questions or comments that are to be reviewed by an administrator. The secure web portal 107 includes the ability to display events, event windows, calendars of events, actionable items, alarms, and notifications from administrators and the Centralized Secure Database 101, and various tools to prioritize and manipulate displays.

An administrative interface 105 allows administrators to access the Administrator Database 104. For example, administrators may use the administrative interface 105 to view information input by investigators. The administrative interface 105 provides such information in various formats, including in customized or standard reports, in searchable tables, and with all personally identifiable information of the participants removed. The administrative interface 105 also allows administrators to send, receive, and reply to communications to one or more investigators. This feature allows an administrator to monitor various aspects of the clinical research trial that may include enrollment, health and safety issues, data collection, and drug accountability, safety, and storage issues.

A Super-Administrator Interface 102 allows an administrator with a high security level clearance to input certain information directly into the Centralized Secure Database 101. For example, such an administrator may use the Super-Administrator Interface 102 to input into the Centralized Secure Database 101 the identification information for the trial sponsor, the clinical research organization, or the investigators. In addition, such an administrator may use the Super-Administrator Interface 102 to input into the Centralized Secure Database 101 information concerning an event such as a description of an event, the date of an event, the dates of future events that relate to an event, and parameters for alarm criteria that will trigger automatic notifications to investigators or administrators.

In this embodiment, two separate communication gateways are also provided: one communication gateway 103 for email warnings, notifications and other communications that are sent to investigators and administrators and a second communication gateway 108 for communications with participants, such as automated email, text, and phone appointment reminders sent to participants and participants' replies to the same.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. Finally, in the foregoing discussion and in the claims, the terms "including" and "comprising" are used in an open-ended fashion, and thus should be interpreted to mean "including, but not limited to . . . ".

What is claimed is:

1. A system for managing research subject or patient events for clinical research trials comprising:
    a centralized secure database;
    an administrator database communicatively connected to said centralized secure database;
    one or more investigator databases communicatively connected to said centralized secure database whereby information residing in said one or more investigator databases is periodically transferred to said centralized secure database and said information is not shared directly between any of said one or more investigator databases;
    a high-clearance interface for accessing said centralized secure database;
    an administrator interface for accessing said administrator database, wherein said administrator database includes information from more than one investigator database;
    an investigator interface for accessing said one or more investigator databases; and
    at least one communication gateway, wherein said investigator interface includes an automated scheduling tool that tracks the progress of participants in a clinical research trial, and wherein said automated scheduling tool identifies the eligibility of prospective participants for participation in a clinical research trial without revealing the personally identifiable information of said prospective participants.

2. A system for managing research subject or patient events for clinical research trials comprising:
    a centralized secure database;
    an administrator database communicatively connected to said centralized secure database;
    one or more investigator databases communicatively connected to said centralized secure database whereby information residing in said one or more investigator databases is periodically transferred to said centralized secure database and said information is not shared directly between any of said one or more investigator databases;
    a high-clearance interface for accessing said centralized secure database;
    an administrator interface for accessing said administrator database, wherein said administrator database includes information from more than one investigator database;
    an investigator interface for accessing said one or more investigator databases; and
    at least one communication gateway, wherein said investigator interface sends automated appointment reminders to participants via said at least one communication gateway in the form of emails, text messages, or phone calls.

3. A system for managing research subject or patient events for clinical research trials comprising:
    a centralized secure database;

an administrator database communicatively connected to said centralized secure database;
one or more investigator databases communicatively connected to said centralized secure database whereby information residing in said one or more investigator databases is periodically transferred to said centralized secure database and said information is not shared directly between any of said one or more investigator databases;
a high-clearance interface for accessing said centralized secure database;
an administrator interface for accessing said administrator database, wherein said administrator database includes information from more than one investigator database;
an investigator interface for accessing said one or more investigator databases; and
at least one communication gateway, wherein said investigator interface sends messages from investigators to participants while restricting the access of said investigators to the contact information of said participants.

4. A system for managing research subject or patient events for clinical research trials comprising:
a centralized secure database;
an administrator database communicatively connected to said centralized secure database;
one or more investigator databases communicatively connected to said centralized secure database whereby information residing in said one or more investigator databases is periodically transferred to said centralized secure database and said information is not shared directly between any of said one or more investigator databases;
a high-clearance interface for accessing said centralized secure database;
an administrator interface for accessing said administrator database, wherein said administrator database includes information from more than one investigator database;
an investigator interface for accessing said one or more investigator databases; and
at least one communication gateway, wherein said at least one communication gateway allows for communication between investigators and administrators and for communication between investigators and participants.

5. A system for managing research subject or patient events for clinical research trials comprising:
a centralized secure database;
an administrator database communicatively connected to said centralized secure database;
one or more investigator databases communicatively connected to said centralized secure database whereby information residing in said one or more investigator databases is periodically transferred to said centralized secure database and said information is not shared directly between any of said one or more investigator databases;
a high-clearance interface for accessing said centralized secure database;
an administrator interface for accessing said administrator database, wherein said administrator database includes information from more than one investigator database;
an investigator interface for accessing said one or more investigator databases; and
at least one communication gateway, wherein said at least one communication gateway allows for communication between investigators and administrators and for communication between investigators and participants, and wherein said communication is automatically stored in said centralized secure database.

6. A system for managing research subject or patient events for clinical research trials comprising:
a centralized secure database;
an administrator database communicatively connected to said centralized secure database;
one or more investigator databases communicatively connected to said centralized secure database whereby information residing in said one or more investigator databases is periodically transferred to said centralized secure database and said information is not shared directly between any of said one or more investigator databases;
a high-clearance interface for accessing said centralized secure database;
an administrator interface for accessing said administrator database, wherein said administrator database includes information from more than one investigator database;
an investigator interface for accessing said one or more investigator databases; and
at least one communication gateway, wherein information entered into said one or more investigator databases is transferred to said centralized secure database and a portion of said information with all personally identifiable information removed is transferred to said administrator database.

7. A system for managing research subject or patient events for clinical research trials comprising:
a centralized secure database;
an administrator database communicatively connected to said centralized secure database;
one or more investigator databases communicatively connected to said centralized secure database whereby information residing in said one or more investigator databases is periodically transferred to said centralized secure database and said information is not shared directly between any of said one or more investigator databases;
a high-clearance interface for accessing said centralized secure database;
an administrator interface for accessing said administrator database, wherein said administrator database includes information from more than one investigator database;
an investigator interface for accessing said one or more investigator databases; and
at least one communication gateway, wherein first limited datasets from said centralized secure database are periodically transferred to said administrator database and second limited datasets from said centralized secure database are periodically transferred to said one or more investigator databases.

8. A method for managing research subject or patient events for clinical research trials comprising:
entering clinical research trial configuration information into a centralized secure database through a high-clearance interface;
entering clinical research trial data into one or more investigator databases through an investigator interface;
periodically transferring said clinical research trial data residing in said one or more investigator databases to said centralized secure database, but not directly between said one or more investigator databases, and periodically transferring limited datasets from said centralized secure database to an administrator database, wherein said administrator database includes information from more than one investigator database;

monitoring and analyzing said limited datasets in said administrator database with an administrator interface;
providing prompts to investigators and participants through at least one communication gateway, wherein said prompts include automated reminders of events for the implementation of a clinical research trial protocol, and
recording said prompts in said centralized secure database.

9. A method for managing research subject or patient events for clinical research trials comprising:
entering clinical research trial configuration information into a centralized secure database through a high-clearance interface;
entering clinical research trial data into one or more investigator databases through an investigator interface;
periodically transferring said clinical research trial data residing in said one or more investigator databases to said centralized secure database, but not directly between said one or more investigator databases, and periodically transferring limited datasets from said centralized secure database to an administrator database, wherein said administrator database includes information from more than one investigator database, and wherein said investigator interface sends messages from investigators to participants while restricting the access of said investigators to the contact information of said participants;
monitoring and analyzing said limited datasets in said administrator database with an administrator interface;
providing prompts to investigators and participants through at least one communication gateway; and
recording said prompts in said centralized secure database.

10. A method for managing research subject or patient events for clinical research trials comprising:
entering clinical research trial configuration information into a centralized secure database through a high-clearance interface;
entering clinical research trial data into one or more investigator databases through an investigator interface;
periodically transferring said clinical research trial data residing in said one or more investigator databases to said centralized secure database, but not directly between said one or more investigator databases, and periodically transferring limited datasets from said centralized secure database to an administrator database, wherein said administrator database includes information from more than one investigator database;
monitoring and analyzing said limited datasets in said administrator database with an administrator interface;
providing prompts to investigators and participants through at least one communication gateway, wherein said at least one communication gateway allows for communication between investigators and administrators and for communication between investigators and participants; and
recording said prompts in said centralized secure database.

11. The method of claim 10 further comprising automatically storing said communication in said centralized secure database.

12. A method for managing research subject or patient events for clinical research trials comprising:
entering clinical research trial configuration information into a centralized secure database through a high-clearance interface;
separating from said clinical research trial data a limited dataset that includes no personally identifiable information;
entering clinical research trial data into one or more investigator databases through an investigator interface;
periodically transferring said clinical research trial data residing in said one or more investigator databases to said centralized secure database, but not directly between said one or more investigator databases, and periodically transferring limited datasets from said centralized secure database to an administrator database, wherein said administrator database includes information from more than one investigator database;
monitoring and analyzing said limited datasets in said administrator database with an administrator interface;
providing prompts to investigators and participants through at least one communication gateway; and
recording said prompts in said centralized secure database.

* * * * *